(12) United States Patent
Nash

(10) Patent No.: US 6,498,287 B2
(45) Date of Patent: Dec. 24, 2002

(54) PEPPER VARIETY

(75) Inventor: Allan Nash, Orinda, CA (US)

(73) Assignee: DNA Plant Technology Corporation, Nogales, AZ (US)

( * ) Notice: Subject to any disclaimer, the term of this patent is extended or adjusted under 35 U.S.C. 154(b) by 0 days.

(21) Appl. No.: 09/792,481

(22) Filed: Feb. 23, 2001

(65) Prior Publication Data

US 2002/0007502 A1 Jan. 17, 2002

Related U.S. Application Data

(60) Provisional application No. 60/184,903, filed on Feb. 25, 2000.

(51) Int. Cl.$^7$ .............................. A01H 5/00; A01H 9/00; A01H 11/00
(52) U.S. Cl. .................. 800/317.1; 800/295; 47/DIG. 1
(58) Field of Search ............................... 800/317.1, 230, 800/295; 426/615; 47/DIG. 1

(56) References Cited

U.S. PATENT DOCUMENTS 5,066,830 A    11/1991    Morrison ..................... 800/230

OTHER PUBLICATIONS

Application for Plant Variety Protection Certificate for Pepper ('Vegi–Sweet'), with Exhibits A—E, U.S. Department of Agriculture, Document No. 8800202.

*Primary Examiner*—Kent L. Bell

(57) ABSTRACT

The present invention is directed to new pepper varieties that bear fruit that are sweet, red, and low-seeded and resemble a Jalapeño pepper in size and shape. Methods of making the plants are also provided.

3 Claims, No Drawings

PEPPER VARIETY

CROSS REFERENCE TO RELATED APPLICATIONS

This application claims priority to U.S. 60/184,903 filed Feb. 25, 2000, which is incorporated herein by reference.

BACKGROUND OF THE INVENTION

Pepper is in the genus Capsicum, which includes the species *Capsicum annuum* and *Capsicum frutescens*. Peppers are cultivated and used around the world as sweet peppers such as the bell pepper; or as pungent chili peppers, jalapeno peppers, and TABASCO peppers (used to make TABASCO sauce); or as a source of dried powders of various colors such as paprika.

The types of cultivated peppers can be differentiated by pungency, fruit shape, and size. Non-pungent peppers used for the fresh market include the large, blocky, thick-fleshed Bell or Stuffing type (e.g., cv.s (cultivars) California Wonder, Yolo Wonder, Keystone Giant and Dulce Italians) and the medium-sized, heart-shaped, thick-fleshed Pimiento type (e.g., cv.s Pimiento, Pimiento Select, Pimiento Perfection, and Super Red Pimiento) peppers, and the long, blunt-ended, thin fleshed Cuban type (e.g., cv.s Cubanelle, and Aconcagua). Mildly pungent peppers used for the fresh market and for processing include the long, heart-shaped, thin-fleshed Ancho type (e.g., cv.s Mexican Chili, Ancho, and Mulato), and the long, blunt-ended, thin-fleshed Tuscan type (e.g., cv. Pepperoncini) peppers. The slightly more pungent Anaheim Chili (e.g., cv.s Anaheim Chili, Sandia, California Chili, Mild California, and New Mexican Chili) which is used mainly for processing has an elongate fruit which tapers to a point and medium flesh thickness. Pungent peppers used in both the fresh market and for processing include the long, cylindrical-thick fleshed Jalapeño (e.g., cv.s Jalapeño and Mild Jalapeño), the small, slender, tapering Serrano (e.g., cv. Serrano), and the irregularly shaped, thin-fleshed Cayenne (e.g., cv.s Cayenne Long Thick, Cayenne Long Slim, and Cayenne Long Red) peppers. In addition to the above *C. annuum* types, there are various *C. frutescens* type peppers (e.g., cv. Tabasco).

SUMMARY OF THE INVENTION

The present invention provides sweet, low-seeded hybrid peppers that resemble a Jalapeño pepper in size and shape. When fully mature, the fruit are red in color, 1¼"–2¾" in length and ¾–1½" in diameter. Brix° measurements are greater than 9.0. Usually, the plants of the invention result from crossing a first inbred pepper plant having low-seeded, Jalapeño-shaped red fruit by a second inbred pepper plant having low-seeded Jalapeño-shaped orange fruit.

In this invention, a sweet, red, low-seeded pepper hybrid is produced. An exemplary line is DNAP 98004 (Pepper seed (*Capsicum annuum*) 98004 deposited under the terms of the Budapest Treaty on Jul. 28, 2000 as ATCC Accession No. PTA-2275 with the American Type Culture Collection in Manassas, Va.). The parental lines are DNAP 89300 (PVP 8800202, Vegi-Sweet), as the female parent and DNAP 94166 as the male parent. The invention also provides pepper fruit and seed produced by such hybrids. In addition, the invention provides pepper seed that can be grown to yield a hybrid plant of the invention.

The invention further provides methods of making a hybrid pepper that is sweet, red, and low-seeded and resembles a Jalapeño pepper in size and shape. The methods comprise crossing a first red-fruited pepper plant that is sweet, low-seeded and resembles a Jalapeño pepper in size and shape with a second orange, fruited pepper plant that is sweet, low-seeded and resembles a Jalapeño pepper in size and shape. F1 plants that are red-fruited, sweet, low-seeded and resemble a Jalapeño pepper in fruit size and shape are then selected.

Both parental lines are produced by crossing and pedigree selection to identify progeny having the desired traits. In particular, both parents should produce fruit that are sweet, low-seeded, and resemble a Jalapeño pepper in size and shape. Preferred lines for this purpose are DNAP 89300 and DNAP 94166.

Definitions

As used herein a first plant "grown from" seed of a second plant includes one that arises directly or indirectly from the seed of the second plant. Thus, the first plant may be an $F_1$ or more removed generation produced by standard breeding techniques using the second plant as parent, so long as the first plant has all the characteristics of the second plant. A first plant has "all the characteristics of" a second plant if it share all the relevant morphological and physiological characteristics of the second plant. For example, in the case of the pepper plants of the invention, the main distinguishing characteristics of the plant are fruit color, sugar content, seed number, and shape, as described here.

The term "Brix°" is used as a measure of sugar content of the fruit of the invention. Brix ° is a standard refractometric measure of sugars. One Brix° unit is approximately 1% sugar by weight. As used here a "sweet" pepper fruit is one having a Brix° reading of at least about 8.0, preferably at least about 9.0.

A pepper fruit that is "Jalapeño pepper in size and shape" is one that has as a generally long, cylindrical shape. Typically, the fruit are between about 1 and about 3 inches in length, usually between about 1.25 inches and about 2.75 inches in length. The fruit are usually between about 0.5 inches and about 2 inches in diameter, usually between about 0.75 inches and about 1.5 inches in diameter.

A "low seeded" fruit is one that comprises less than about 30 seed, usually less than about 25 seed.

DESCRIPTION OF THE SPECIFIC EMBODIMENTS

The hybrid plants of the invention result from a cross of parental lines that bear fruit that are sweet, low-seeded, and resemble a Jalapeño pepper in fruit size and shape. Preferred lines for this purpose are DNAP 89300 and DNAP 94166. DNAP 89300 (PVP 8800202) has been identified in the segregating populations of a cross between Sweet Bell (PVP 8700124) and P.I. 379183. DNAP 94166 has been identified in the segregating populations of a cross between Corona and DNAP 89382 (a sister selection to DNAP 89300). The F1 generation is then examined for the presence of red fruit that are sweet, low-seeded and resembling a Jalapeño pepper in fruit size and shape. Sweetness is measured in the laboratory by measuring Brix° levels. Low-seeded refers to approximately less than or equal to 30 seed per fruit. The red color is caused by alleles that are dominant.

This hybrids of the invention have a compact semi-erect habit, with intermediate branching. Leaves are elliptic and medium-large in size. Foliage is a medium-green color. There is one flower per leaf axil. The corolla is white and the style is slightly shorter than the stamens in length. Fruit are smooth, pendant, and slightly blunt at the apex. Fruit have 1–2 locules and oblong in shape. The pedicel is medium in length and straight to slightly curved. Seed are yellow and there are less than 30 per fruit.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A hybrid pepper plant grown from seed deposited with the ATCC under Accession No. PTA-2275.
2. Fruit harvested from the plant of claim 1.
3. Hybrid seed which can be grown to yield a pepper plant of claim 1.

* * * * *